United States Patent
Bronkalla et al.

(10) Patent No.: US 10,726,948 B2
(45) Date of Patent: Jul. 28, 2020

(54) MEDICAL IMAGING DEVICE- AND DISPLAY-INVARIANT SEGMENTATION AND MEASUREMENT

(71) Applicant: INTERNATIONAL BUSINESS MACHINES CORPORATION, Armonk, NY (US)

(72) Inventors: Mark D. Bronkalla, Hartland, WI (US); Sun Young Park, San Diego, CA (US); Murray A. Reicher, San Diego, CA (US); Dustin Sargent, San Diego, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 200 days.

(21) Appl. No.: 15/836,185

(22) Filed: Dec. 8, 2017

(65) Prior Publication Data

US 2019/0180860 A1 Jun. 13, 2019

(51) Int. Cl.
| | |
|---|---|
| *G16H 30/20* | (2018.01) |
| *A61B 5/00* | (2006.01) |
| *G06T 7/11* | (2017.01) |
| *G16H 30/40* | (2018.01) |
| *G06T 7/136* | (2017.01) |
| *G06T 7/00* | (2017.01) |

(52) U.S. Cl.
CPC .............. *G16H 30/20* (2018.01); *A61B 5/004* (2013.01); *A61B 5/7267* (2013.01); *G06T 7/11* (2017.01); *G16H 30/40* (2018.01); *A61B 5/0073* (2013.01); *A61B 5/444* (2013.01); *A61B 5/7425* (2013.01); *G06T 7/0016* (2013.01); *G06T 7/136* (2017.01); *G06T 2207/10081* (2013.01); *G06T 2207/20081* (2013.01); *G06T 2207/20101* (2013.01); *G06T 2207/30064* (2013.01); *G06T 2207/30096* (2013.01)

(58) Field of Classification Search
CPC ......... G06T 7/0016; G06T 7/11; G06T 7/136; G06T 2207/30096; A61B 5/004; A61B 5/0073; A61B 5/444; A61B 5/7425; G16H 30/20; G16H 30/40
USPC ......................................... 382/128, 131, 294
See application file for complete search history.

(56) References Cited

U.S. PATENT DOCUMENTS

| | | | |
|---|---|---|---|
| 8,675,931 B2 | 3/2014 | Ye et al. | |
| 8,885,926 B2 | 11/2014 | Seung et al. | |
| 9,002,083 B2* | 4/2015 | Fox ..................... | G06F 19/3418 382/128 |
| 9,053,574 B2 | 6/2015 | Ernvik et al. | |

(Continued)

*Primary Examiner* — Daniel G Mariam
(74) *Attorney, Agent, or Firm* — Erik Huestis; Stephen Kenny; Foley Hoag, LLP

(57) ABSTRACT

Medical imaging device- and display-invariant segmentation and measurement is provided. In various embodiments, a plurality of medical images is read from a data store. Metadata of each of the plurality of medical images is read. The metadata identifies an image acquisition device associated with each of the plurality of medical images. Based on the plurality of medical images and the metadata of each of the plurality of images, a learning system is trained to determine one or more image correction parameters. The one or more image correction parameters optimize segmentation of the plurality of medical images.

20 Claims, 15 Drawing Sheets

(56) References Cited

U.S. PATENT DOCUMENTS

| | | | | |
|---|---|---|---|---|
| 2005/0049497 A1* | 3/2005 | Krishnan | ............... | G06F 19/321 |
| | | | | 600/437 |
| 2012/0290324 A1* | 11/2012 | Ribbing | ................ | G06F 19/321 |
| | | | | 705/3 |
| 2013/0336553 A1* | 12/2013 | Buisseret | ............... | G06T 7/0012 |
| | | | | 382/128 |
| 2018/0350075 A1* | 12/2018 | Grimmer | ................... | G06T 7/41 |
| 2019/0205606 A1* | 7/2019 | Zhou | .................... | G06K 9/0014 |

\* cited by examiner

US 10,726,948 B2

MEDICAL IMAGING DEVICE- AND DISPLAY-INVARIANT SEGMENTATION AND MEASUREMENT

BACKGROUND

Embodiments of the present disclosure relate to imaging devices and/or systems, and more specifically, to imaging devices and/or systems that can compensate for image acquisition and algorithm variations.

BRIEF SUMMARY

According to embodiments of the present disclosure, methods of and computer program products for providing display-invariant segmentation are provided. A plurality of medical images is read from a data store. Metadata of each of the plurality of medical images is read. The metadata identifies an image acquisition device associated with each of the plurality of medical images. Based on the plurality of medical images and the metadata of each of the plurality of images, a learning system is trained to determine one or more image correction parameters. The one or more image correction parameters optimize segmentation of the plurality of medical images.

DETAILED DESCRIPTION

Figure 1A:
FIGS. 1A-B depict a comparison of traditional CT images for lung nodule under different window width and level settings.

Assessment of medical imaging, such as those for tumor growth and treatment response assessment, generally relies on the physician's visual review and manual measurements. This process is highly influenced by variations in image acquisition devices, imaging protocols, display parameters, and the physician's subjective preferences. Variations in image reconstruction kernels, acquisition pixel and slice spacing, contrast agent dose amount, light power, noise, and contrast level have significant effects on tumor segmentation and measurement results.

To address, these and other shortcomings of alternative approaches, embodiments of the present disclosure provide robust system and methods for medical image processing capable of adjusting for and incorporating parameter variations in image acquisition or segmentation algorithm. Thus, consistent segmentation and measurement may be provided across various imaging conditions by correcting for the effects of variations between imaging systems and segmentation algorithms.

In various embodiments, an optimal transformation of each type of input data is learned. For example, adjustments to window width and level, noise and smoothing filters, and other image characteristics may be learned. In some embodiments, learning may be performed without knowledge of the specific segmentation algorithm being applied. In various embodiments, optimal segmentation algorithm parameters may be learned, using an API exposing parameter data types and valid ranges. Likewise, the choice of optimal segmentation algorithm may be learned. In some embodiments, global optimization or machine learning methods, such as genetic algorithms, may be applied to learn these parameters.

In some embodiments, a feature vector is provided to a learning system. Based on the input features, the learning system generates one or more outputs. In some embodiments, the output of the learning system is a feature vector.

In some embodiments, the learning system comprises a SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

Any one of these methods may be used for the robust imaging system described herein, alone or in combination with each other or other methods known to one of ordinary skill in the art. Equivalent methods or modifications may also be used, according to common knowledge in the art. Optionally, users of the system may provide feedback (e.g., online feedback, real-time feedback, etc.) into at least one of the above-described methods, in order to continuously improve the system.

In various embodiments, medical images may be stored in a Picture Archiving and Communication System (PACS), a medical imaging system that provides storage and access to images from multiple modalities. In many heathcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

Figure 1B:

With reference now to FIGS. 1A-B, an exemplary CT image of a lung nodule was acquired and displayed under different window and level settings. Such parameter differences increase the apparent size of the circled lesion in FIG. 1A compared to FIG. 1B, leading to potentially different measurement results and thus different tumor diagnosis or assessment for the same tissue sample.

Figure 2A:
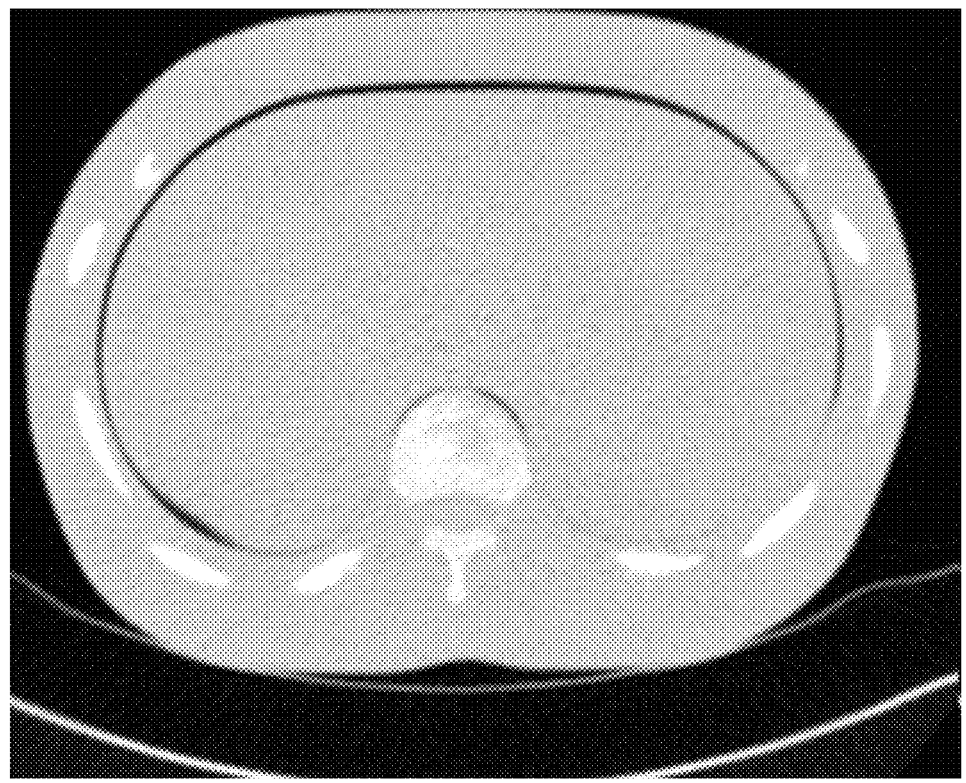
FIGS. 2A-B depict a comparison of traditional CT phantom data images for lung tissue under different exposure settings.
Figure 2B:
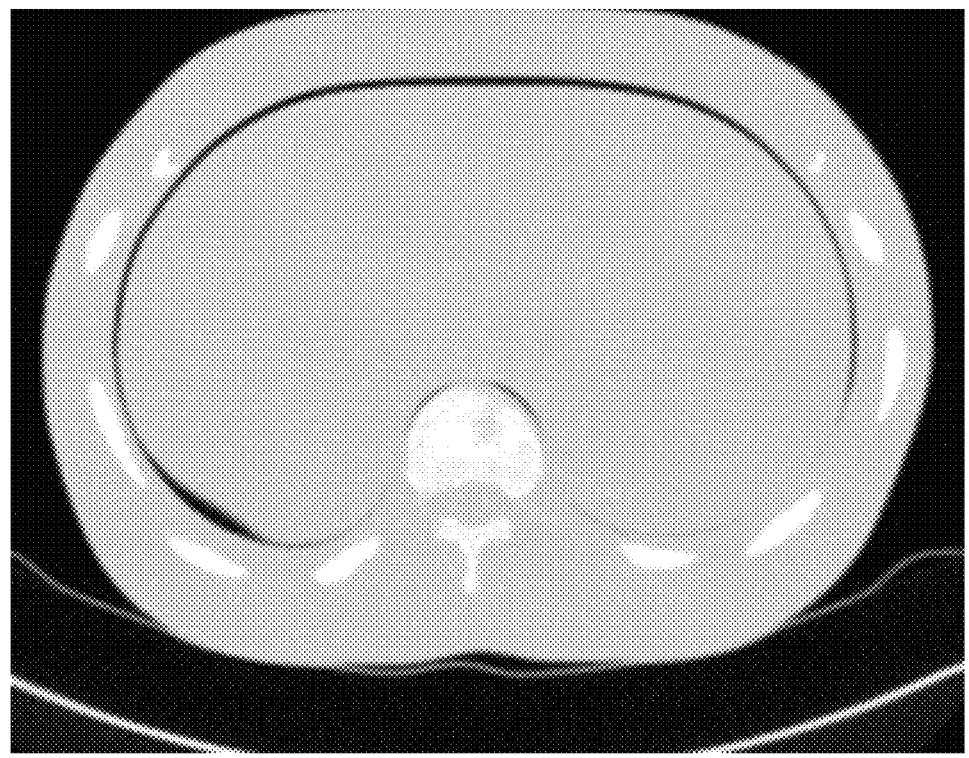
Figure 3A:
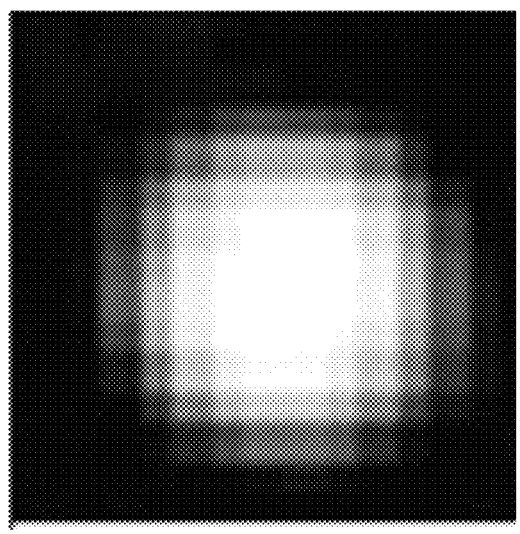
FIGS. 3A-D depict an exemplary synthetic lung nodule image (FIG. 3A), which may lead to variance in subjective boundary annotation due to intensity changes in the boundary (FIGS. 3B-D).
Figures 3B, 3C, 3D:
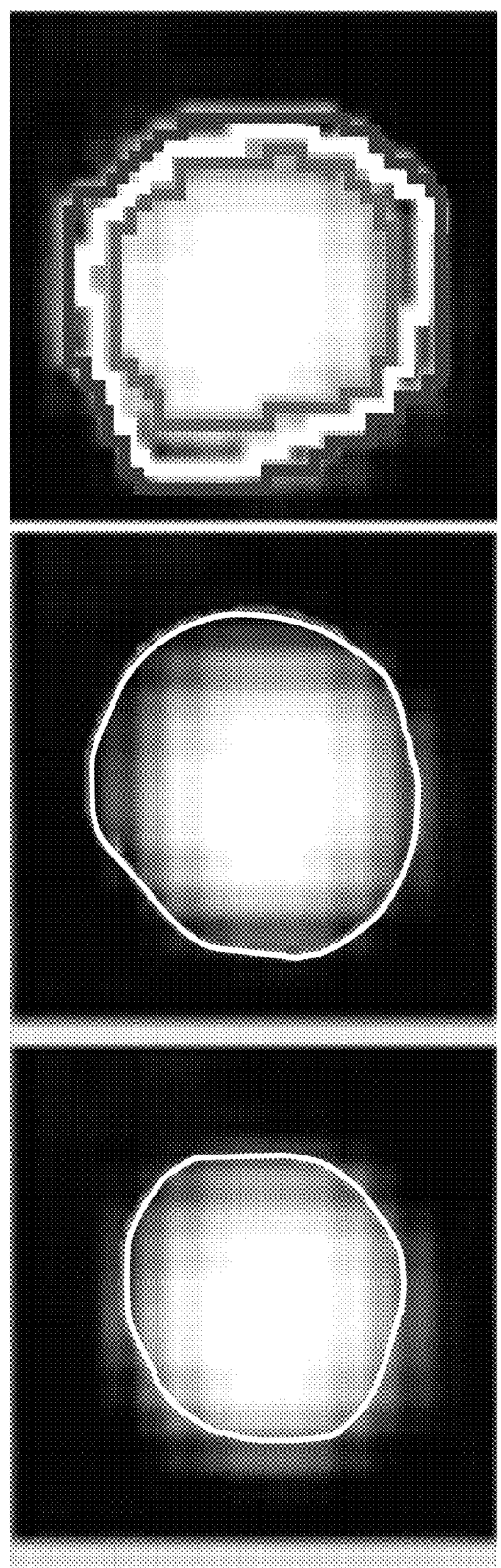

With reference now to FIGS. 2A-B, an exemplary CT phantom data image of the lungs was acquired using the same scanner model with different acquisition parameters. Exemplary scanner parameters include slice spacing, convolution kernel, reconstruction diameter, and exposure. With the other parameters maintained constant, the image in FIG. 2A was captured with exposure 20 while the image of FIG. 2B was captured with exposure 200. As shown in FIG. 2, the noise level, contrast, and edge sharpness of CT images are all influenced by such change in exposure, potentially leading to different measurement, diagnosis, and assessment for the same tissue sample.

With reference now to FIGS. 3A-D, an exemplary synthetic lung nodule image was captured, appearing to have a fuzzy boundary. Different device users may manually draw the boundary differently when annotating, leading to potential variations in measurement, diagnosis, and assessment. Even for a single user, different imaging settings, such as image exposure and intensity may still result in different measurement, diagnosis, and assessment. Exacerbating this risk for inconsistency, studies have shown significant variation in contours drawn by different radiologists on the same lesion. Moreover, differences in imaging conditions can cause even greater variations in the appearance of the lesion that can drastically affect measurements.

Figure 4:
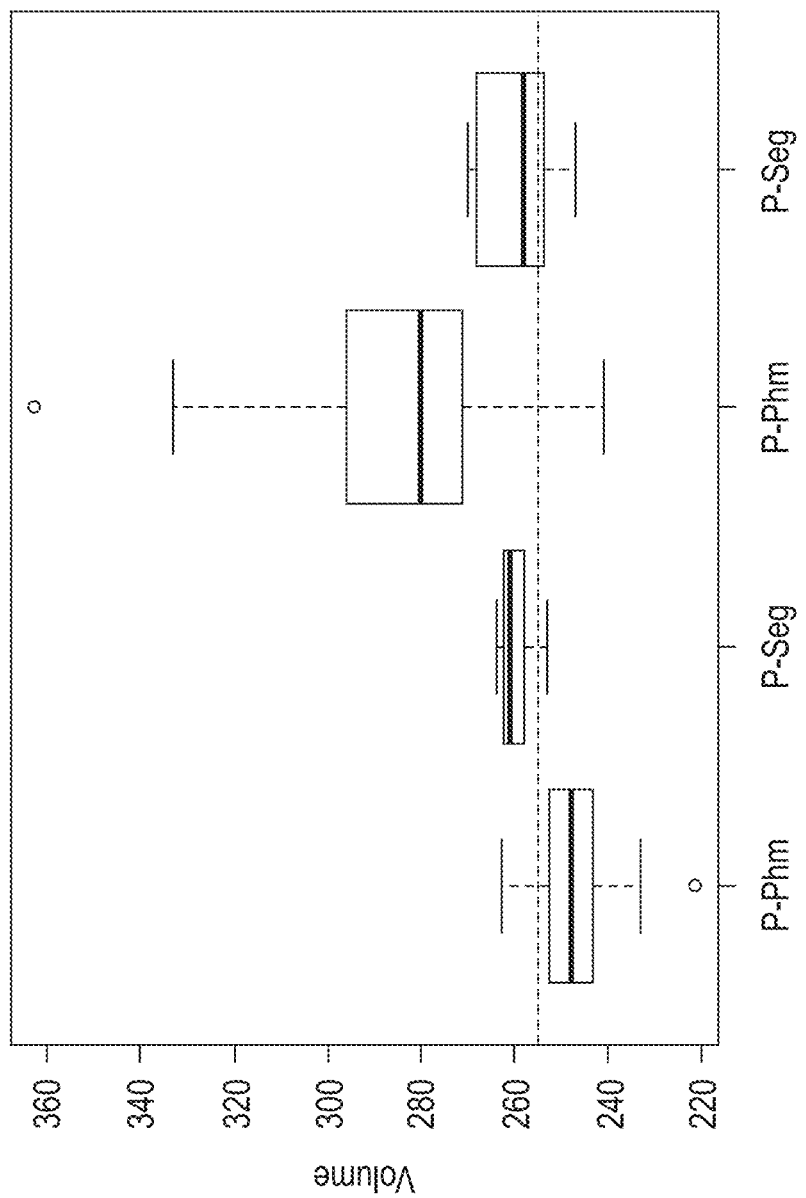
FIG. 4 depicts an exemplary volume measurement differences between phantom data on a Philips Mx8000 IDT 16 scanner and Siemens Definition scanner.

With reference now to FIG. 4, an exemplary phantom lung nodule image was acquired and a variation in the volume measurement for the lung nodule with devices under different imaging settings is shown. The horizontal dotted line represents the ground truth measurement of 255 µl. The first boxplot (P-Phm) shows a range of segmentation results from intensity thresholding with a target of 100 HU acquired on Philips Mx8000 IDT 16 scanners. The second boxplot (P-Seg) shows the range of segmentation results obtained using a gradient-based segmentation algorithm on images acquired using the same Philips scanner. The third boxplot (S-Phm) shows a range of segmentation results from intensity thresholding with a target of 100 HU acquired on a Siemens Definition scanner. The fourth boxplot (P-Seg) shows a range of segmentation results using a gradient based segmentation algorithm on the same images from the Siemens scanner. As shown in FIG. 4, the variation introduced by the different devices caused a change of up to 20% in the apparent intensity and volume of a lesion of known size. These effects along with variations in the segmentation algorithm can cause confusion as to whether or not changes in measurement values reflect actual changes in the lesion size.

In various embodiments of the present disclosure, a system is provided that can compensate for image acquisition and algorithm variations and produce consistent segmentation and measurement results across various imaging conditions. An exemplary system may learn segmentation parameters that provide accurate measurement results (e.g., lesion diameter, lesion volume, etc.) from one or more sources. Similarly, the choice of segmentation algorithm may be learned. For example, in some embodiments, phantom data analysis with objects of known size may be used in training. Similarly, expert-annotated clinical data may be used in training. In various embodiments, these data sources are used alone or in combination with each other or with at least additional training sets. In some embodiments, images from each source are acquired or viewed with different devices and display parameters. In some embodiments, at least two sources are acquired or viewed with the same device or same display parameters. Segmentation and measurements may be performed using the learned optimal segmentation parameters for a given device/display/modality/etc. rather than relying on the user's current selections. Results may be reported along with the expected error given the current device and display parameters.

In addition to optimization on the basis of scanner type and processing parameters, various embodiments also enable optimization on the basis of anatomical location. For example, many segmentation algorithms may be tuned to specific body parts and modalities. In such cases, the present disclosure allows dynamic selection of the appropriate segmentation tool and the parameters for that tool. The subject anatomy of a given image or study may be determined from image metadata, for example as included in a DICOM header.

It will be appreciated that a variety of image correction parameters may be optimized as set forth herein. In addition to window width/level and smoothing filters as described above, intensity normalization (e.g., between prior and current images or between test data and phantom images), noise removal, resampling to uniform spacing or to match training data, equalization of the contrast dose effects by simulation, signal to noise ratio correction, or parameters of various additional image filters may be optimized.

Figure 5:
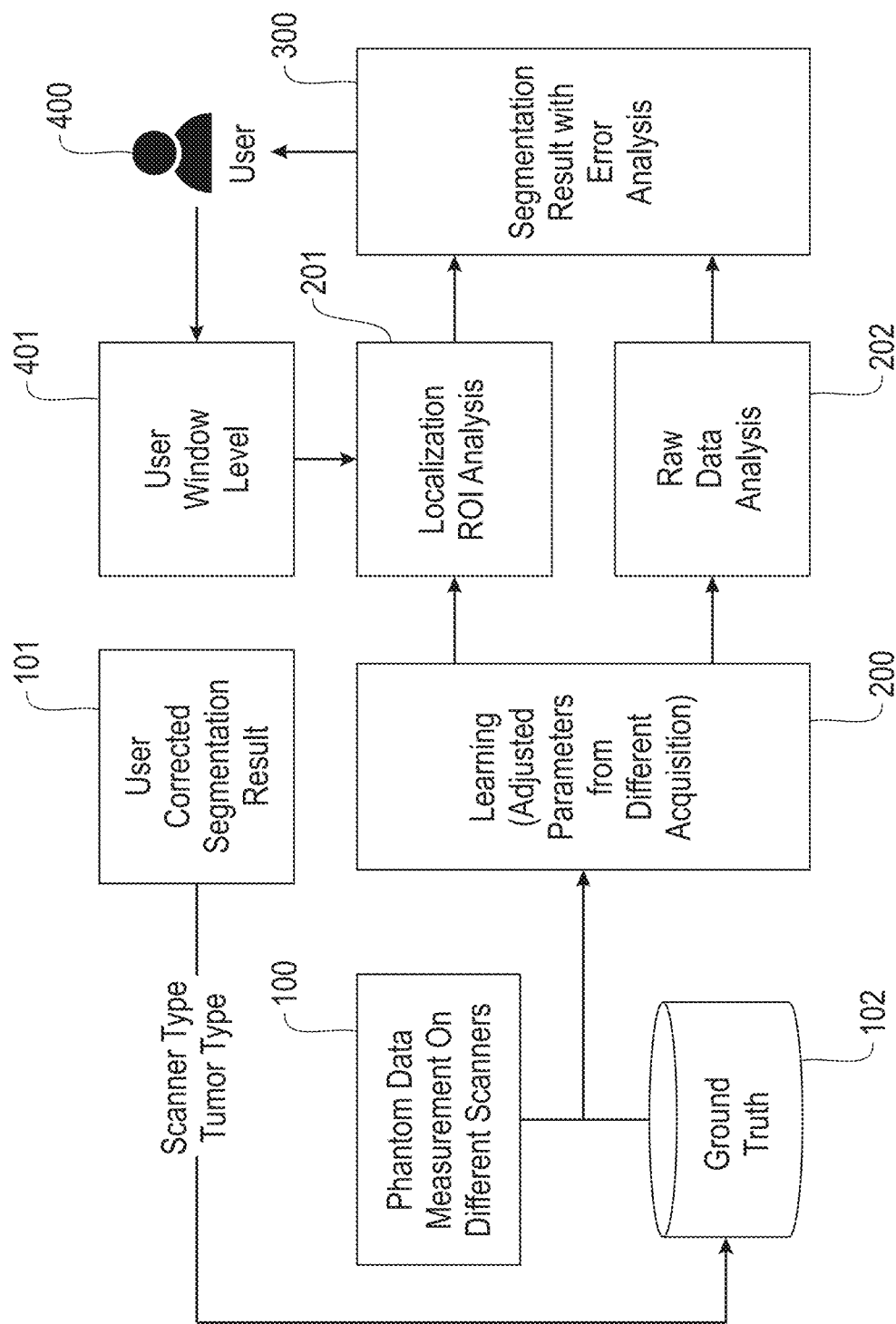
FIG. 5 depicts a computing node comprising an exemplary imaging system according to embodiments of the present disclosure.

Referring now to FIG. 5, a schematic of an example of a computing node comprising an exemplary imaging system described herein is shown. The original phantom data measurement on different scanners 100 is combined with optional user corrected segmentation result 101 (according to the same scanner type and/or the tumor type for acquiring the phantom data) to produce the Ground truth 102 for the following learning phase 200, in which at least one of adjusted parameters based on different data acquisitions is incorporated. The resulting localization region of interest (ROI) analysis 201 and raw data analysis 202 are used to produce segmentation result with error analysis 300, which is further used as by the user 400 to fine-tune the settings and/or parameter, such as user window level 401, and to provide feedback to the localization ROI analysis 201. During the exemplary processes in FIG. 5, the lesion segmentation algorithm will perform an analysis using the user-applied window level settings and the original raw data.

In accordance with an aspect of the present disclosure, the lesion's boundary intensity may be adjusted according to different imaging device (e.g. scanner) types. The adjustment parameters may be learned using one or more processes, such as phantom data analysis and clinical studies (for animal, patient, etc.) and user-corrected boundary information including vessel removals. Additionally or alternatively, various embodiments may include user-suggested parameters (e.g., window-level), multiple segmentation results or expected variation and error levels depending on the different acquisition systems employed. Accordingly, the present disclosure is not constrained or limited by the size of the lesion, and provides an error analysis, as described below.

Figure 6:
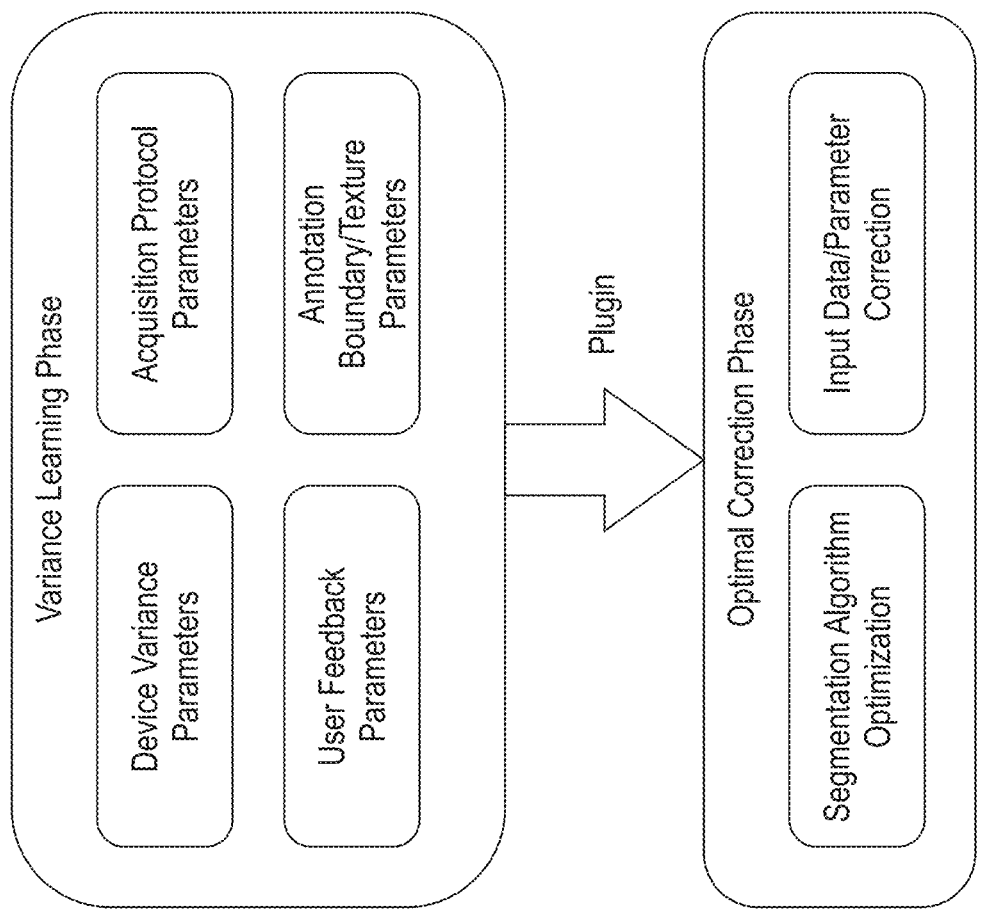
FIG. 6 depicts a combined diagram of an exemplary imaging system (including a learning phase and an application phase) according to embodiments of the present disclosure.

Referring now to FIG. 6, a combined diagram of an exemplary imaging system of the present disclosure is shown. The exemplary imaging system illustrated includes a learning phase and an application phase. As shown in FIG. 6, an exemplary learning phase for imaging variance may incorporate parameters such as device variance, acquisition protocol, user feedback, annotation boundary/texture, etc. In some embodiments each of these parameter types are included in the learning phase, whereas in other embodiments only select parameter types are incorporated. An exemplary optimal correction phase may be used together with the learning phase, including an optimization processes such as segmentation algorithm optimization, input data/parameter correction, etc. In some embodiments, a flexible plugin feature may be incorporated between the learning phase and the optimal correction phase. The plugin can include general features known in the art, or specific features designed for a particular scanner/sample, while also allowing for other imaging parameters to be added.

Figure 7:
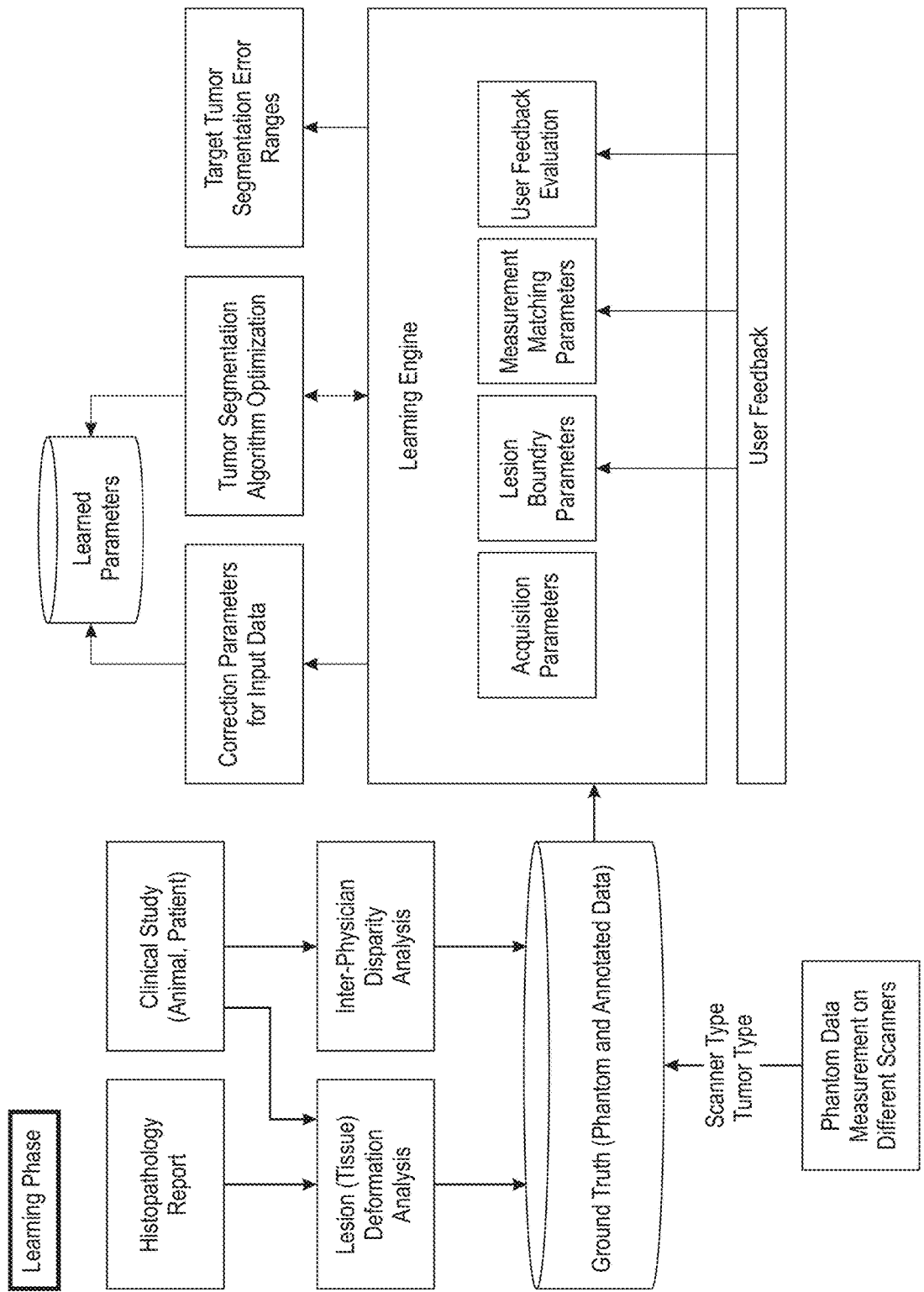
FIG. 7 depicts a more detailed block diagram of an exemplary learning phase of an exemplary imaging system according to embodiments of the present disclosure.

Referring now to FIG. 7, a more detailed block diagram of an exemplary learning phase for the imaging system of the present disclosure is shown. Specifically, a large, varied database of annotated and phantom ground truth data may be used to learn an optimal transformation for each type of input data to optimize the accuracy of the ground truth measurements using the given segmentation algorithm. Non-phantom data ground truth may be obtained from histopathology reports with tissue mapping back to the original tissue, manual annotations performed by physicians, and derived from clinical studies. In some embodiments, parameters of the segmentation algorithm may also be optimized for each input type. The results of the training phase may be the set of learned parameters, and expected error ranges for each type of data. For purpose of illustration and not limitation, an exemplary learning phase may use a training database containing 5 lung CT nodule examples with ground truth masks labeling the nodules, while the segmentation algorithm has one real numbered threshold with acceptable values between 0 and 1. In an exemplary embodiment, for the display parameters to be learned (e.g., the optimal window width and window level), the optimal threshold and window width/level values are determined by optimization with a genetic algorithm. The genetic algorithm having an objective function which is the sum of the Dice index of the algorithm's results and the ground truth on the 5 lung nodule masks. Though training databases of alternative size can be employed, if so desired.

Figure 8:
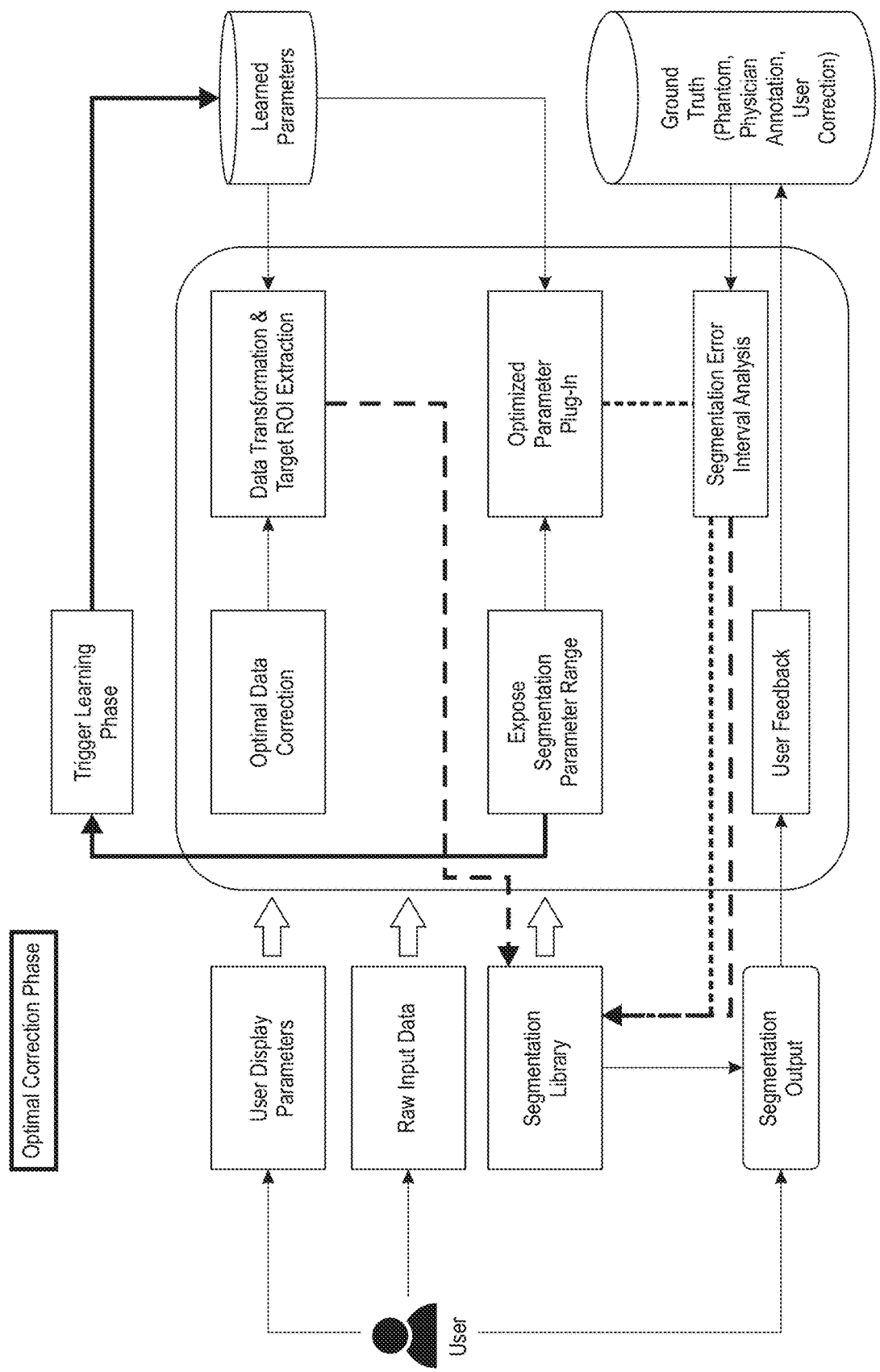
FIG. 8 depicts a more detailed block diagram of an exemplary application phase of an exemplary imaging system according to embodiments of the present disclosure.

Referring now to FIG. 8, a more detailed block diagram of an exemplary application phase for the imaging system of the present disclosure is shown. Specifically, the input display settings, raw data, and segmentation algorithm are provided by the user application. An optimal transformation to the input data is applied based on the learned "input correction parameters" from the learning phase. In some embodiments, optimal segmentation parameters are also retrieved from the learned database. Segmentation output is returned along with an expected error analysis derived from the training database. Additionally, the user provides feedback as to the correctness of the segmentation which is returned to the learning phase along with the input data and display/segmentation parameters. The optimization function can be modified with a new example, and some additional iterations performed to update the learned parameters accounting for the new example.

Figure 9:
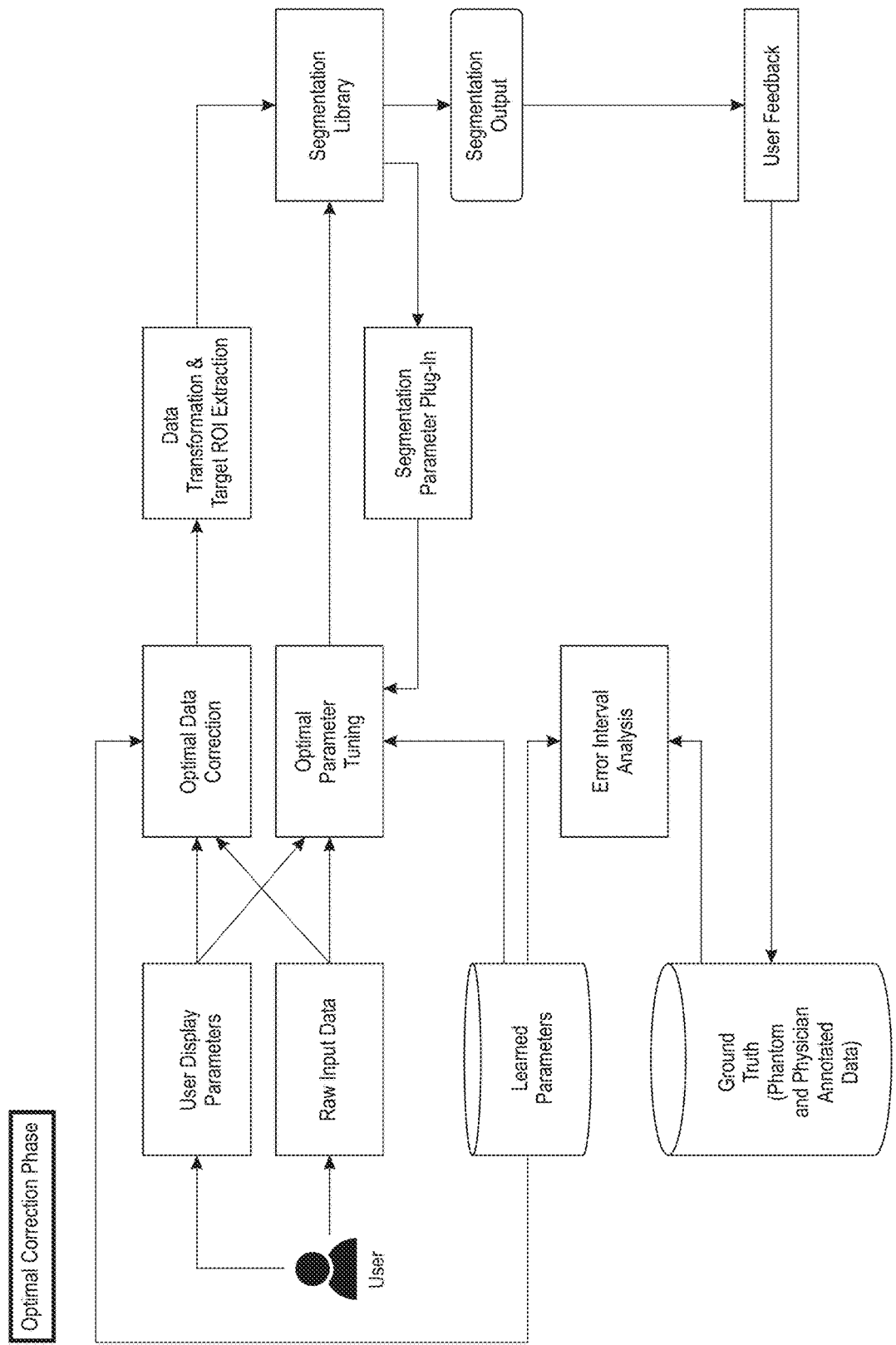
FIG. 9 depicts a block diagram of another exemplary application phase of an exemplary imaging system according to embodiments of the present disclosure.

Referring now to FIG. 9, another block diagram of an exemplary application phase for the imaging system described herein is shown. In this exemplary embodiment, the input display settings and raw data are provided by the user application. An optimal transformation to the input data is applied and the segmentation algorithm is accessed along with a segmentation parameter plugin. The error interval analysis is performed with inputs from the learned parameters and ground truth data, and segmentation output is returned.

Figure 10:
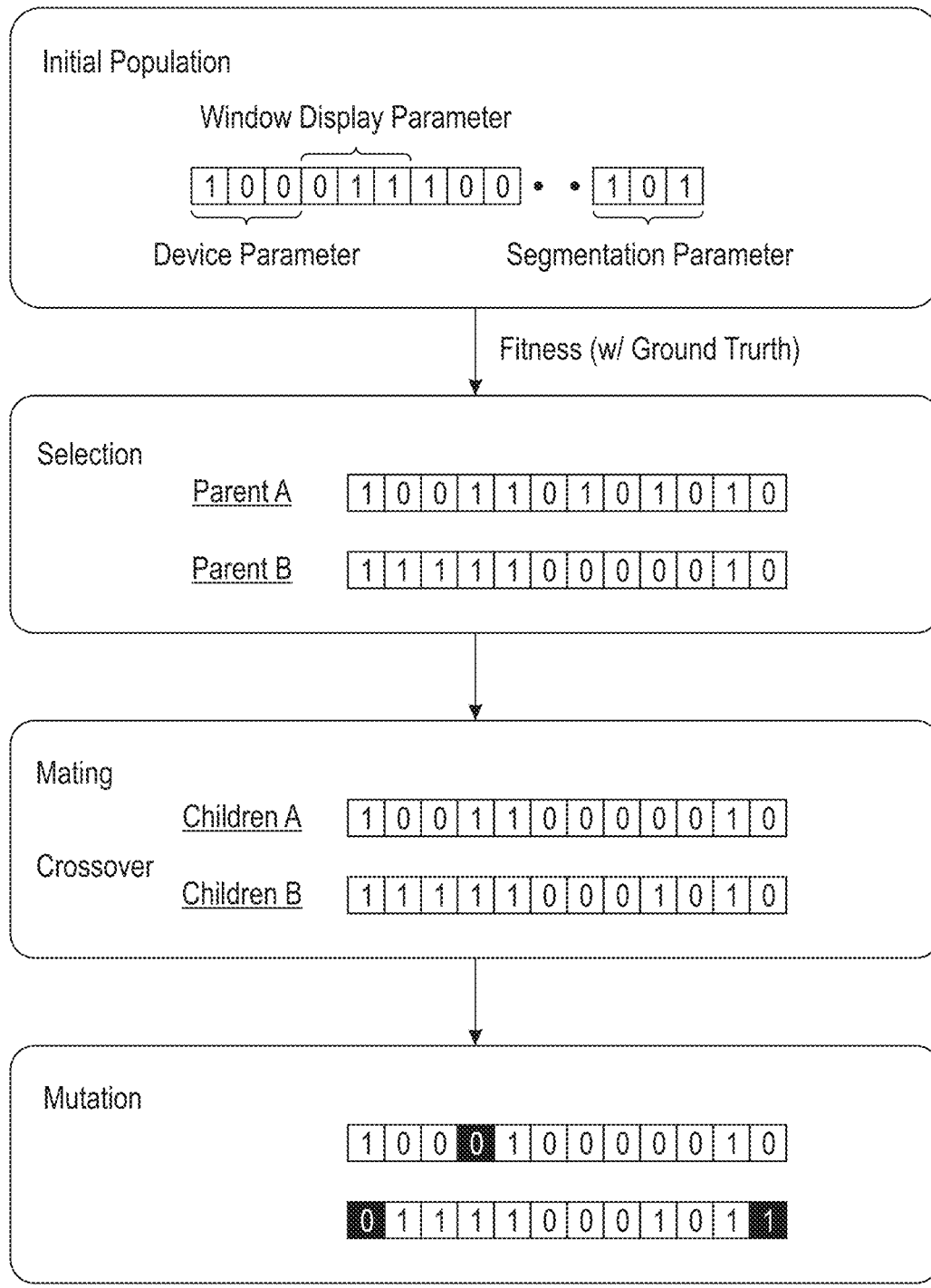
FIG. 10 depicts an exemplary optimization process with an genetic algorithm for an exemplary imaging system according to embodiments of the present disclosure.

Referring now to FIG. 10, for purpose of illustration and not limitation, an exemplary genetic algorithm may be used to simultaneously optimize the display and algorithm parameters for the imaging system of the present disclosure is shown. Starting from an initial population of parameter sets, the genetic algorithm may simulate several generations and ultimately select the best performing set on the ground truth database. In accordance with another aspect of the present disclosure, the process described herein can also determine which parameters have no impact on the segmentation results, and those parameters can be thrown out from consideration.

The imaging system of the current disclosure may comprise a computing node performing at least one of phases and/or functions as illustrated in FIGS. 5-9. Such computing node, or any parts thereof, is only one example of a suitable computing node and is not intended to suggest any limitation as to the scope of use or functionality of embodiments of the disclosure described herein. Regardless, the computing node described herein is capable of being implemented and/or performing any of the functionality set forth hereinabove.

Figure 11:
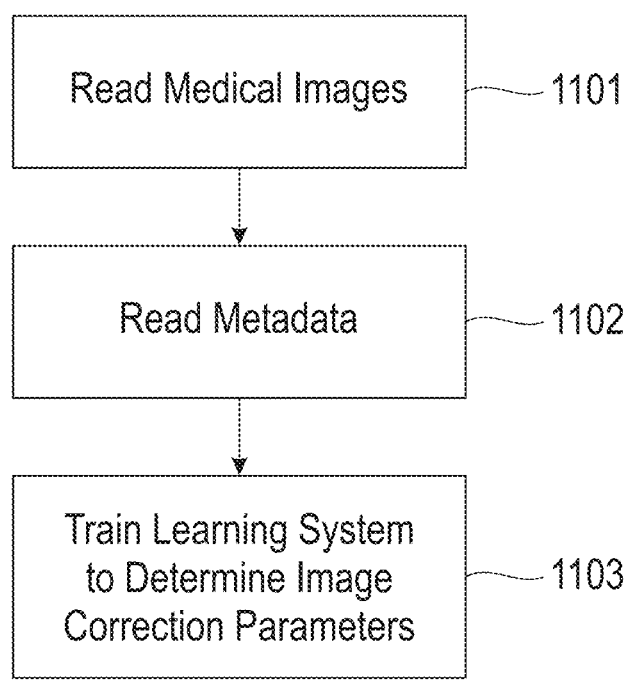
FIG. 11 illustrates a method of providing display-invariant segmentation are provided according to embodiments of the present disclosure.

Referring now to FIG. 11, a method for providing display-invariant segmentation is illustrated according to embodiments of the present disclosure. At 1101, a plurality of medical images is read from a data store. Metadata of each of the plurality of medical images is read. The metadata identifies an image acquisition device associated with each of the plurality of medical images. Based on the plurality of medical images and the metadata of each of the plurality of images, a learning system is trained to determine one or more image correction parameters. The one or more image correction parameters optimize segmentation of the plurality of medical images.

It will be appreciated that the above disclosure provides for optimizing image parameters, choice of segmentation algorithm, and segmentation algorithm parameters. In this way, variations in segmentation of the same data may be minimized. In particular, variations in segmentation may arise from change in imaging device, change in segmentation software, or change in user reviewing the image.

Calibration of individual devices alone does not address the segmentation accuracy issues across multiple devices, different user settings, different algorithms, different training data, or different disease states.

Figure 12:
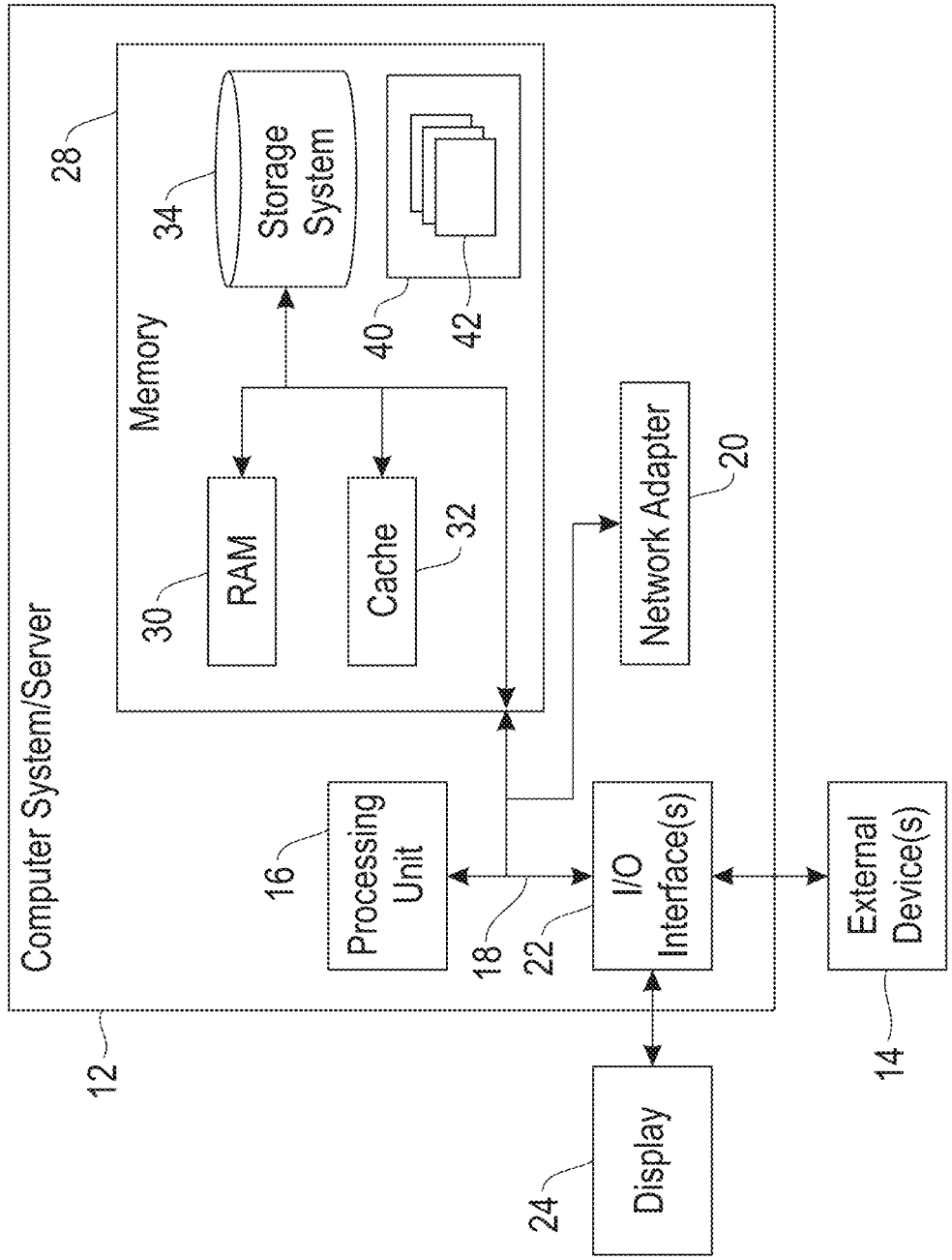
FIG. 12 depicts a computing node according to embodiments of the present disclosure.

Referring now to FIG. 12, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 12, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   reading a plurality of medical images from a data store;
   reading metadata of each of the plurality of medical images, the metadata identifying an image acquisition device associated with each of the plurality of medical images;
   based on the plurality of medical images and the metadata of each of the plurality of images, training a learning system to determine one or more image correction parameters, the one or more image correction parameters adapted to optimize the plurality of medical images for segmentation.

2. The method of claim 1, further comprising:
   after training, applying the learning system to determine one or more image correction parameters of an additional medical image.

3. The method of claim 2, further comprising:
applying the determined one or more image correction parameters to the additional medical image to thereby generate a corrected medical image; and
segmenting the corrected medical image.

4. The method of claim 1, wherein training the learning system comprises:
determining a segmentation of each of the plurality of medical images;
comparing the segmentation to ground truth.

5. The method of claim 1, further comprising:
training the learning system to determine one or more segmentation parameters, the one or more segmentation parameters optimizing segmentation of the plurality of medical images.

6. The method of claim 5, further comprising:
determining an expected error range of the segmentation.

7. The method of claim 1, wherein the one or more image correction parameters includes window, level, noise, or smoothing.

8. The method of claim 1, wherein the metadata further identifies one or more image acquisition parameter associated with each of the plurality of medical images.

9. The method of claim 1, wherein the one or more image correction parameters includes exposure, intensity, image reconstruction kernels, acquisition pixel and slice spacing, contrast agent dose amount, light power, noise, or contrast level.

10. The method of claim 1, wherein the learning system comprises a genetic algorithm.

11. The method of claim 1, further comprising:
further training the learning system based on user-generated segmentation.

12. The method of claim 1, wherein the metadata further comprises an indication of a subject anatomy of the plurality of medical images.

13. A system comprising:
a datastore;
a computing node comprising a computer readable storage medium having program instructions embodied therewith, the program instructions executable by a processor of the computing node to cause the processor to perform a method comprising:
reading a plurality of medical images from the data store;
reading metadata of each of the plurality of medical images, the metadata identifying an image acquisition device associated with each of the plurality of medical images;
based on the plurality of medical images and the metadata of each of the plurality of images, training a learning system to determine one or more image correction parameters, the one or more image correction parameters adapted to optimize the plurality of medical images for segmentation.

14. A computer program product for providing display-invariant segmentation, the computer program product comprising a computer readable storage medium having program instructions embodied therewith, the program instructions executable by a processor to cause the processor to perform a method comprising:
reading a plurality of medical images from a data store;
reading metadata of each of the plurality of medical images, the metadata identifying an image acquisition device associated with each of the plurality of medical images;
based on the plurality of medical images and the metadata of each of the plurality of images, training a learning system to determine one or more image correction parameters, the one or more image correction parameters adapted to optimize the plurality of medical images for segmentation.

15. The computer program product of claim 14, the method further comprising:
after training, applying the learning system to determine one or more image correction parameters of an additional medical image.

16. The computer program product of claim 15, the method further comprising:
applying the determined one or more image correction parameters to the additional medical image to thereby generate a corrected medical image; and
segmenting the corrected medical image.

17. The computer program product of claim 14, wherein training the learning system comprises:
determining a segmentation of each of the plurality of medical images;
comparing the segmentation to ground truth.

18. The computer program product of claim 14, the method further comprising:
training the learning system to determine one or more segmentation parameters, the one or more segmentation parameters optimizing segmentation of the plurality of medical images.

19. The computer program product of claim 18, the method further comprising:
determining an expected error range of the segmentation.

20. The computer program product of claim 14, the method further comprising:
further training the learning system based on user-generated segmentation.

* * * * *